United States Patent
Truscott

[19]

[11] Patent Number: 5,997,543
[45] Date of Patent: Dec. 7, 1999

[54] SURGICAL INSTRUMENTATION

[75] Inventor: James William Truscott, Swindon, United Kingdom

[73] Assignee: Biomet Limited, United Kingdom

[21] Appl. No.: 09/027,161

[22] Filed: Feb. 20, 1998

[30] Foreign Application Priority Data

Feb. 21, 1997 [GB] United Kingdom .................. 9703637

[51] Int. Cl.$^6$ .................................................. A61B 17/56
[52] U.S. Cl. .................................. 606/86; 606/82; 606/88
[58] Field of Search ................................. 606/79, 82, 86, 606/87, 88, 89

[56] References Cited

U.S. PATENT DOCUMENTS

| | | |
|---|---|---|
| 2,696,817 | 12/1954 | Prevo . |
| 3,638,243 | 2/1972 | Campbell, Jr. et al. . |
| 3,656,186 | 4/1972 | Dee . |
| 3,708,805 | 1/1973 | Scales et al. . |
| 3,728,742 | 4/1973 | Averill et al. . |
| 3,739,403 | 6/1973 | Nicolle . |
| 3,772,709 | 11/1973 | Swanson . |
| 3,816,854 | 6/1974 | Schlein . |
| 3,852,831 | 12/1974 | Dee . |
| 3,886,600 | 6/1975 | Kahn et al. . |
| 3,886,601 | 6/1975 | Findlay . |
| 3,919,725 | 11/1975 | Swanson et al. . |
| 3,939,496 | 2/1976 | Ling et al. . |
| 3,990,116 | 11/1976 | Fixel et al. . |
| 3,990,117 | 11/1976 | Pritchard et al. . |
| 4,008,495 | 2/1977 | Cavendish et al. . |
| 4,024,588 | 5/1977 | Janssen et al. . |
| 4,038,704 | 8/1977 | Ring . |
| 4,057,858 | 11/1977 | Helfet . |
| 4,106,128 | 8/1978 | Greenwald et al. . |
| 4,129,902 | 12/1978 | Harmon . |
| 4,131,956 | 1/1979 | Treace . |
| 4,224,695 | 9/1980 | Grundei et al. . |
| 4,242,758 | 1/1981 | Amis et al. . |

(List continued on next page.)

FOREIGN PATENT DOCUMENTS

| | | |
|---|---|---|
| 0 466 659 A2 | 1/1992 | European Pat. Off. . |
| 0 720 834 A2 | 7/1996 | European Pat. Off. . |
| 2 215 610 | 9/1989 | United Kingdom . |

OTHER PUBLICATIONS

Biomet Ltd. brochure entitled "Kudo Elbow System", pp. 1–12, Copyright 1989.

Chapter 12, entitled "Capitellocondylar Total Elbow Arthroplasty", by Fredrick C. Ewald from Master Techniques In Orthopaedic Surgery, The Elbow, Raven Press, Ltd., pp. 209–230, Copyright 1994.

N. Blewitt, FRCS, and J. Pooley, MD, FRCS, "An anatomic study of the axis of elbow movement in the coronal plane: Relevance to component alignment in elbow arthroplasty", Copyright, 1994 by Journal of Shoulder and Elbow Surgery, pp. 151–158.

Orthopedic Equipment Company, Inc. brochure entitled "Stanmore Total Elbow Replacement", 4 pages, Copyright 1978.

Osteonics Corp. brochure entitled "Linked Semi–Constrained Osteonics Total Elbow Prostheses", pp. 1–13, cover page and 4 additional sheets, Copyright 1989.

Zimmer brochure entitled "Coonrad/Morrey Total Elbow", pp. 1–12, Copyright 1989, 1992, 1993.

*Primary Examiner*—Michael Buiz
*Assistant Examiner*—Daphna Shai
*Attorney, Agent, or Firm*—Harness, Dickey & Pierce, P.L.C.

[57] ABSTRACT

A surgical instrument for aligning a surgical tool includes a tool guide in which is provided an opening for receiving and guiding a portion of the surgical tool and a bone engaging element which is adapted to engage a particular region of a bone.

The bone engaging element has a bone engaging surface which has a known orientation relative to the opening in the tool guide. Consequently, when the bone engaging element engages the bone, the opening in the tool guide is correctly aligned with the bone. In a preferred embodiment, the instrumentation is adapted for resecting the distal end of a humerus and the bone engaging element engages the posterior cortex of the distal end of the humerus.

16 Claims, 3 Drawing Sheets

U.S. PATENT DOCUMENTS

| | | |
|---|---|---|
| 4,261,064 | 4/1981 | Helfet . |
| 4,280,231 | 7/1981 | Swanson . |
| 4,293,963 | 10/1981 | Gold et al. . |
| 4,301,552 | 11/1981 | London . |
| 4,378,607 | 4/1983 | Wadsworth . |
| 4,383,337 | 5/1983 | Volz et al. . |
| 4,467,801 | 8/1984 | Whiteside . |
| 4,538,306 | 9/1985 | Dörre et al. . |
| 4,624,250 | 11/1986 | Saunders et al. . |
| 4,686,978 | 8/1987 | Wadsworth . |
| 4,718,414 | 1/1988 | Saunders . |
| 4,822,364 | 4/1989 | Inglis et al. . |
| 4,841,975 | 6/1989 | Woolson . |
| 4,927,422 | 5/1990 | Engelhardt . |
| 5,030,237 | 7/1991 | Sorbie et al. . |
| 5,042,983 | 8/1991 | Rayhack . |
| 5,129,908 | 7/1992 | Petersen ................. 606/86 |
| 5,234,433 | 8/1993 | Bert et al. . |
| 5,314,484 | 5/1994 | Huene . |
| 5,376,121 | 12/1994 | Huene et al. . |
| 5,445,640 | 8/1995 | Johnson et al. ................. 606/86 |
| 5,514,143 | 5/1996 | Bonutti et al. ................. 606/79 |
| 5,601,565 | 2/1997 | Huebner . |
| 5,628,749 | 5/1997 | Vendrely et al. ................. 606/86 |
| 5,720,752 | 2/1998 | Elliot et al. ................. 606/79 |

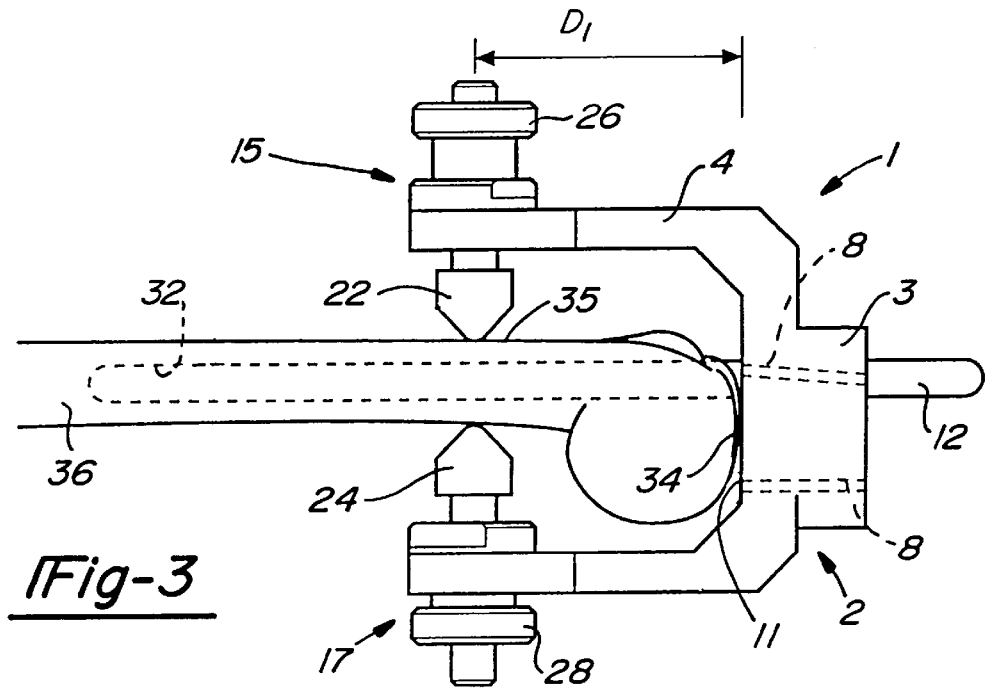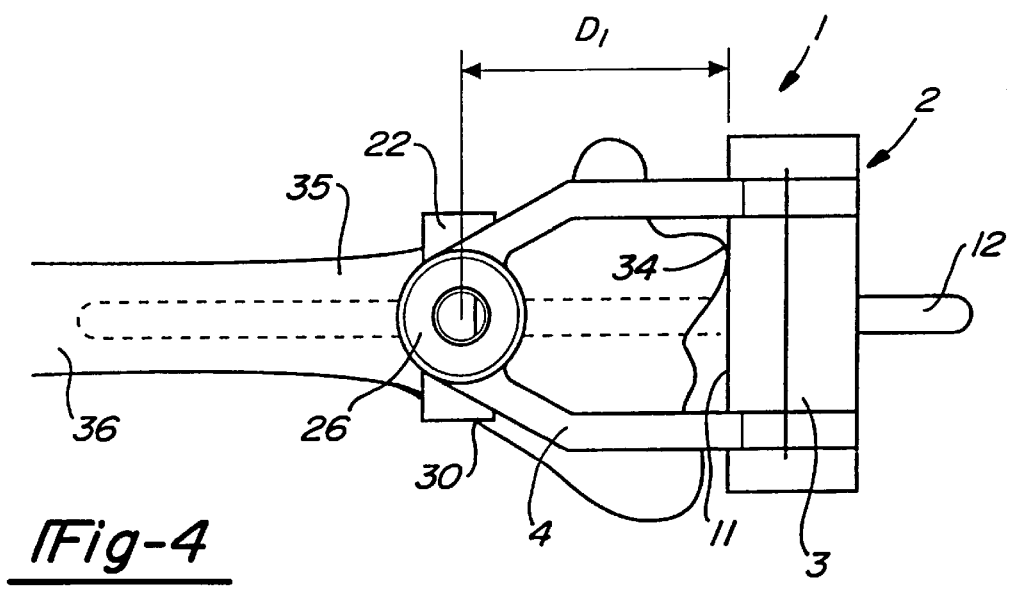

SURGICAL INSTRUMENTATION

BACKGROUND OF THE INVENTION

1. Field of the Invention

This invention relates to instrumentation for aligning a surgical tool, and primarily, although not exclusively relates to instrumentation for use in resecting the distal end of a humerus.

2. Discussion of the Related Art

When implanting a total joint prosthesis, it is necessary to resect the ends of the bones which meet at the joint. In the past, resecting has been carried out by eye and relied almost exclusively on the skill of the surgeon. More recently, instrumentation has been produced for resecting the femur or tibia for installation of a total knee prosthesis. Such instrumentation comprises a jig to which is fitted a rod. The rod is inserted into a bore drilled into the intramedullary canal and provides alignment of the jig with the longitudinal axis of the bone. One or more openings are provided in the jig for insertion of a drill bit or saw blade.

Although this conventional instrumentation provides reasonable alignment with the longitudinal axis of the bone, it does not provide rotational alignment of the jig about the longitudinal axis of the bone, so that the surgeon must have considerable skill and experience before he can carry out an accurate bone resection.

The problems of using the conventional instrumentation are accentuated if the distal end of the humerus is damaged by injury or disease, as it is not possible to use the distal end surface as an accurate reference to locate the normal axis of joint movement. The present invention seeks to address these problems.

SUMMARY OF THE INVENTION

According to a first aspect of the present invention there is provided instrumentation for aligning a surgical tool. The instrumentation includes a tool guide in which is provided an opening for receiving and guiding a portion of the surgical tool and a bone engaging element which is adapted to engage a side of a bone. The bone engaging element has a bone engaging surface which has a known orientation relative to the opening in the tool guide, such that when the bone engaging element engages the bone, the opening in the tool guide is correctly aligned with the bone.

Preferably the tool guide is provided with a bone engaging surface which engages the end of the bone during a resecting operation.

Preferably the distance between the bone engaging surface of the bone engaging element and the bone engaging surface of the tool guide is set prior to attachment of the instrumentation to the bone. This distance may be fixed at the time the instrumentation is manufactured or may be adjustable.

In one embodiment of instrumentation in which the distance is adjustable, the bone engaging element is releasably slidable along an arm connected to the tool guide. Preferably the arm is integrally formed with the tool guide.

The tool guide may be provided with a rod which is inserted into a bore in the intramedullary canal during resection.

The guide opening in the tool guide may comprise a slot for receiving the blade of a saw or may comprise a bore for receiving the shank of a drill. A plurality of guide openings may be provided in the tool guide and may comprise a combination of slots and bores.

The bone engaging element is preferably elongated and when engaging a bone extends substantially transverse to the longitudinal axis of the bone.

In a preferred embodiment, the instrumentation comprises a pair of clamping mechanisms which are adapted to engage opposite sides of the bone, the bone engaging element being connected to one of the clamping mechanisms.

Preferably, the instrumentation is used for aligning a surgical tool for the resecting of an end of a bone. In an embodiment adapted for resecting the distal end of a humerus, the bone engaging element engages the posterior cortex of the distal humerus and the distance between the bone engaging surface of the bone engaging element and the bone engaging surface of the tool guide is adjustable between about 30 mm to about 40 mm. Preferably, the distance is fixed at about 35 mm.

According to a second aspect of the present invention, there is provided instrumentation for aligning a surgical tool during the resecting of an end of a bone. The instrumentation includes a tool guide in which is provided an opening for receiving and guiding a portion of the surgical tool and a pair of clamping mechanisms which are adapted to engage opposite sides of the bone. At least one of the clamping mechanisms being provided with a bone engaging element which is adapted to engage a particular region of the bone and has a bone engaging surface which has a known orientation relative to the opening in the tool guide, such that when the clamping mechanisms are tightened onto the bone, the opening in the tool guide is at a predetermined rotational orientation with respect to the longitudinal axis of the bone.

BRIEF DESCRIPTION OF THE DRAWINGS

For a better understanding of the present invention and to show how it may be carried into effect, reference will now be made, by way of example, to the accompanying drawings, in which:

FIG. 3 is a view on one side of the instrumentation of FIG. 1 when fitted to the distal end of a humerus;

FIG. 4 is a view from above of the instrumentation of FIG. 1 when fitted to the distal end of a humerus.

DETAILED DESCRIPTION OF THE PREFERRED EMBODIMENT(S)

The following description of the preferred embodiments concerning a surgical instrument for aligning a surgical tool are merely exemplary in nature and are not intended to limit the invention or its application or uses. Moreover, while the detailed description refers to the use of the surgical instrument in connection with a distal end of a humerus, those skilled in the art would readily recognize that the surgical instrument may be utilized with various other surgical procedures as well.

Figure 1:
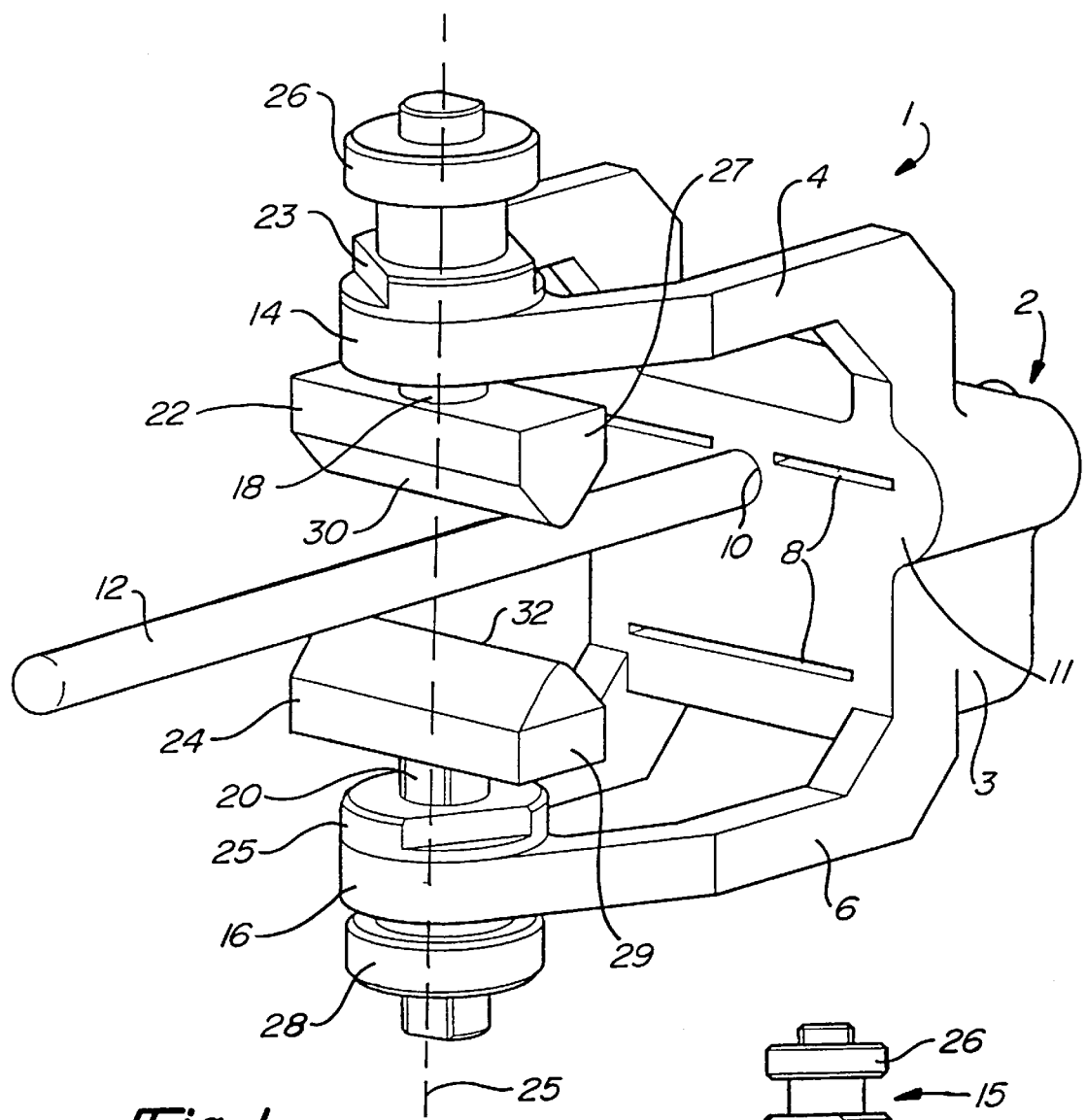
FIG. 1 is a perspective view of instrumentation for aligning a bone saw during resecting of the distal end of a humerus according to the teachings of a first preferred embodiment of the present invention.
Figure 2:
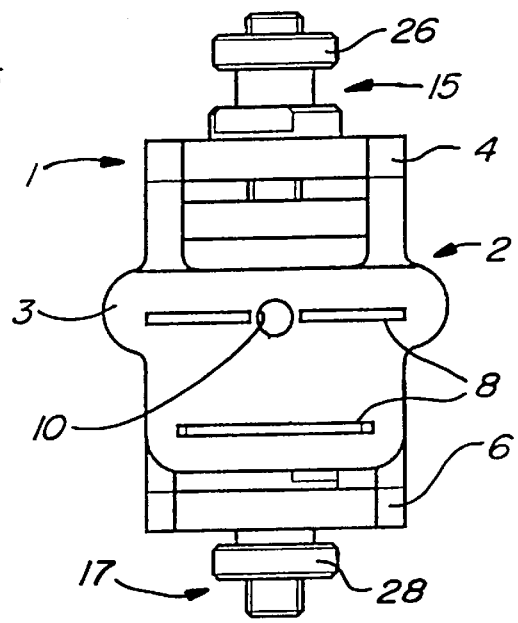
FIG. 2 is a rear view of the instrumentation of FIG. 1.

Referring to the drawings, FIGS. 1 and 2 are views of a surgical instrument 1 for aligning a bone saw with the distal end of a humerus according to the teachings of a first preferred embodiment of the present invention. The surgical instrument 1 comprises a tool guide 2 having a base 3 integrally formed with an opposing pair of arms or clamping members 4, 6 that extend relatively perpendicular to the base 3. Slots or openings 8 which are rectangular in cross-section and are adapted to receive a blade of a bone saw extend through the width of the base 3 of the tool guide 2 along predetermined cutting planes which are aligned relative to a bone received by the surgical instrument 1.

Between the slots 8 is provided a bore 10 which slidably receives a cylindrical intramedullary rod 12. The intramedullary rod 12 extends from a bone engaging surface 11 of the tool guide 2 between the arms or clamping members 4, 6.

The cantilevered free ends 14, 16 of the clamping members 4, 6 are provided with openings or bores (not shown) to adjustably retain a pair of clamping mechanisms 15, 17. The clamping mechanisms 15, 17 include shanks 18 and 20 which pass through the bores and are coupled to respective bone engaging elements 22, 24.

The shanks 18, 20 are slidable or adjustable along a common axis 25 so that the bone engaging elements 22, 24 can be brought closer together or moved further apart, and are fixed in position by means of respective collets 23, 25 operated by finger wheels 26, 28.

The bone engaging elements 22, 24 are of elongate form and taper from a broad base portion 27, 29 to a narrow bone engaging surface or edge 30, 32, respectively.

Referring to FIGS. 3 and 4, the operation of the surgical instrument 1 in relation to a distal end of a humerus 36 is shown. A bore 32 is first drilled along the intramedullary canal from the distal end 34 of a humerus 36 which is to be resected along the predetermined cutting planes. The finger wheels 26, 28 of the clamping mechanisms 15, 17 are then unscrewed, so that the bone engaging elements 22, 24 can be moved apart sufficiently to accommodate the humerus 36. The tool guide 2 is placed onto the humerus 36 with the intramedullary rod 12 removed, such that the bone engaging surface 11 of the base 3 of the tool guide 2 engages the distal end 34 of the humerus 36. The rod 12 is then pushed through the bore 10 passing through the base 3 of the tool guide 2 and into the bore 32 in the intramedullary canal of the humerus 36. The bone engaging elements 22, 24 are then brought together along axis 25 so that the edges 30, 32 of the bone engaging elements 22, 24 are brought into contact with the cortex of the distal end 34 of the humerus 36.

Anatomical studies have established a relationship between the posterior cortex 35 of the distal end 34 of the humerus 36 and the axis of movement of the elbow joint with reference to the coronal plane. Referring to FIG. 4, with the distance $d_1$ between the bone engaging surface 11 of the tool guide 2 and the bone engaging edge 30 of the upper bone engaging element 22 set at about 35 mm, the axis of movement of the elbow joint with reference to the coronal plane will be parallel to the posterior cortex 35 of the distal end 34 of humerus 36 and consequently the bone engaging edge or line 30 of the upper bone engaging element 22 will itself be parallel to the axis of movement of the elbow joint with reference to the coronal plane. By arranging the slots 8 in the tool guide 2 such that they extend in planes parallel to the bone engaging edge 30 of the upper bone engaging element 22, insertion of a bone saw (not shown.) through the slots 8 will result in extremely accurate resection of the distal end 34 of the humerus 36, so that when a prosthetic implant is attached to the resected bone, the axis of the movement of the artificial joint with reference to the coronal plane will coincide exactly or substantially exactly with the axis of movement of the natural joint prior to the operation.

As shown in FIG. 4, the bone engaging element 22 is shown extending substantially transverse to the longitudinal axis of the humerus 36 such that the opening 8 is at a predetermined rotational orientation will respect to the longitudinal axis of the bone.

Figure 5:
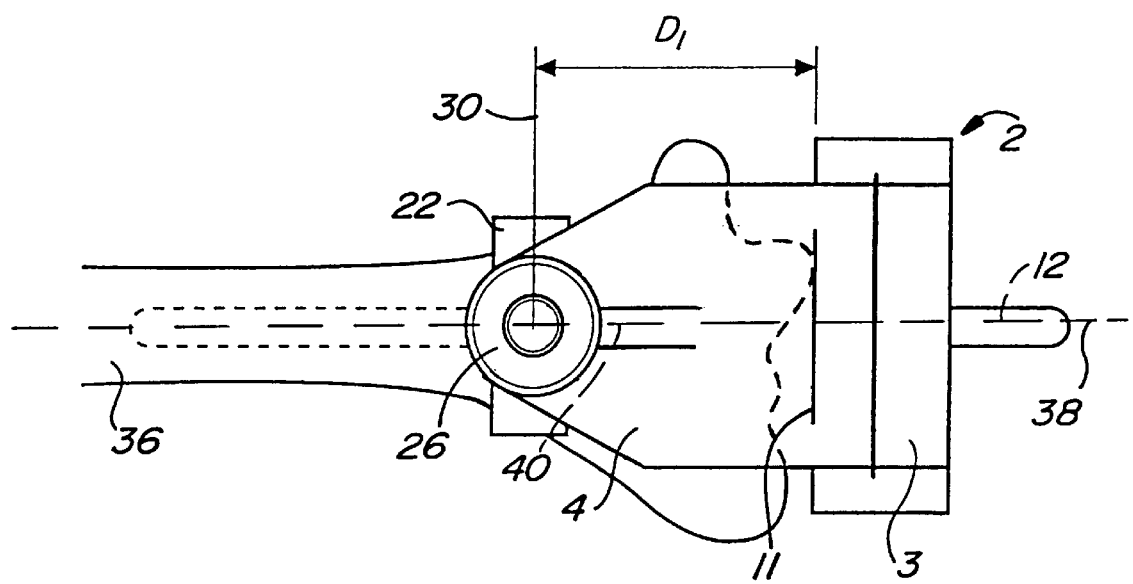
FIG. 5 is a view from above of the instrumentation when fitted to the distal end of a humerus according to the teachings of a second preferred embodiment of the present invention.

In an alternate embodiment shown in FIG. 5, at least the upper bone engaging element 22 is slidably mounted to the arm or clamping member 4, so that the upper bone engaging element 22 can be slid along a line or axis 38 substantially parallel to the intramedullary rod 12 and the distance $d_1$ between the bone engaging edge 30 of the bone engaging element 22 and the bone engaging surface 11 of the tool guide 2 can be adjusted to accommodate for variations in the dimensions of the humerus 36 from patient to patient. However it has been found that in most cases if the distance $d_1$ in FIGS. 4 and 5 is set at about 35 mm, this is appropriate for most patients and that an adjustable range between about 30 mm to about 40 mm will cover the vast majority of patients.

The adjustability of the position of the upper bone engaging element 22 is provided by forming a groove or track 40 in the upper clamping member 4 along which the shank 18 of the upper bone engaging element 22 can slide. In this embodiment, tightening of the finger wheels 26, 28 will not only set the relative separation of the bone engaging elements 22, 24, but will also set the distance between one or more of these elements relative to the bone engaging surface 11 of the tool guide 2. In other words, both the upper clamping member 4 and the lower clamping member 6 may include a track 40 to slidably retain the clamping mechanisms 15, 17.

In addition, instead of a single bore 10 through the tool guide 2, a pair of offset bores may be provided such that the tool guide 2 could be used on either a left or right humerus 36, simply by inserting the intramedullary rod 12 in the appropriate bore.

The surgical instrument 1 is preferably made of stainless steel or titanium, but any appropriate material with sufficient stiffness and strength and which is suitable for autoclaving may also be used.

The foregoing discussion discloses and describes merely exemplary embodiments of the present invention. One skilled in the art will readily recognize from such discussion, and from the accompanying drawings and claims, and that various changes, modifications and variations can be made therein without departing from the spirit and scope of the invention.

What is claimed is:

1. A surgical instrument for aligning a surgical blade during resection of a portion of a bone, said surgical instrument comprising:

a tool guide having a base and a first arm extending substantially from a first end of said base and a second arm extending substantially from a second end of said base, said first end being opposite said second end, said base defining a blade guide for receiving and guiding a portion of the surgical blade; and a first clamping mechanism extending from said first arm and a second clamping mechanism extending from said second arm, said first and second clamping mechanisms adapted to engage opposite sides of the bone, at least one of said clamping mechanisms being provided with a bone engaging element which is adapted to engage a particular region of the bone with a bone engaging surface which has a known orientation relative to said blade guide in said base, wherein when said first and second clamping mechanisms are tightened onto the bone, said blade guide in said base is at a predetermined rotational orientation with respect to a longitudinal axis of the bone.

2. The surgical instrument as defined in claim 1, wherein said tool guide is provided with a second bone engaging surface at said base which engages an end of the bone.

3. The surgical instrument as defined in claim 2, wherein a distance between said bone engaging surface of said bone engaging element and said second bone engaging surface of said tool guide is adjustable.

4. The surgical instrument as defined in claim 3, wherein said bone engaging element is releasably slidable along one of said first and second arms to adjust said distance.

5. The surgical instrument as defined in claim 4, wherein said first and second arms are integrally formed with said tool guide.

6. The surgical instrument as defined in claim 2, wherein said tool guide aligns a surgical blade for resecting a distal end of a humerus, whereby a distance between said bone engaging surface of said bone engaging element and said second bone engaging surface of said tool guide is between about 30 mm to about 40 mm.

7. The surgical instrument as defined in claim 6, wherein said distance is about 35 mm.

8. The surgical instrument as defined in claim 6, wherein said bone engaging element engages a posterior cortex of the distal end of the humerus.

9. The surgical instrument as defined in claim 1, wherein said tool guide is provided with an intramedullary rod.

10. The surgical instrument as defined in claim 1, wherein a plurality of guide openings are provided.

11. The surgical instrument as defined in claim 1, wherein said bone engaging element is elongated and when engaging the bone extends substantially transverse to a longitudinal axis of the bone.

12. The surgical instrument as defined in claim 1, wherein said bone engaging surface of said bone engaging element is aligned substantially parallel to an axis of movement of a joint of the bone.

13. A surgical instrument for aligning a surgical blade during resection of a joint end of a bone, said surgical instrument comprising:

a tool guide having a base and a first cantilevered arm extending substantially from a first end of said base and a second cantilevered arm extending substantially from a second end of said base, said first end being opposite said second end, said first and second arms extending substantially perpendicular from said base, said base defining a blade guide for receiving and guiding a portion of the surgical blade and a first bone engaging surface; and a first clamping mechanism movably coupled to said first arm, said first clamping mechanism including a bone engaging element having a second bone engaging surface operable to engage the bone along a line substantially parallel to a joint axis of rotation of the joint end of the bone, wherein when said second bone engaging surface of said bone engaging element engages the bone along said line substantially parallel to said joint axis, said blade guide defined in said base of said tool guide is at a predetermined rotational orientation with respect to a longitudinal axis of the bone.

14. The surgical instrument as defined in claim 13, further comprising a second clamping mechanism movably coupled to said second arm.

15. The surgical instrument as defined in claim 13, wherein said first clamping mechanism is slidably adjustable relative to said first bone engaging surface.

16. The surgical instrument as defined in claim 13, wherein said blade guide defined in said base of said tool guide extends parallel to the second bone engaging surface of the bone engaging element.

* * * * *